United States Patent
Nakanishi et al.

(10) Patent No.: US 8,315,351 B2
(45) Date of Patent: Nov. 20, 2012

(54) SYSTEM AND METHOD FOR TOMOGRAPHIC RECONSTRUCTION UTILIZING CIRCULAR TRAJECTORY AND SCANOGRAM TO REDUCE ARTIFACTS

(75) Inventors: Satoru Nakanishi, Tochigi-ken (JP); Yu Zou, Naperville, IL (US); Aleksandr Zamyatin, Buffalo Grove, IL (US); Michael D. Silver, Northbrook, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/178,094

(22) Filed: Jul. 7, 2011

(65) Prior Publication Data

US 2011/0317805 A1    Dec. 29, 2011

Related U.S. Application Data

(63) Continuation of application No. 12/238,079, filed on Sep. 25, 2008, now abandoned.

(60) Provisional application No. 61/001,110, filed on Oct. 31, 2007.

(51) Int. Cl.
    *A61B 6/03* (2006.01)

(52) U.S. Cl. ............................ 378/4; 378/19; 382/131

(58) Field of Classification Search ................ 378/4, 19; 382/128–131
See application file for complete search history.

(56) References Cited

U.S. PATENT DOCUMENTS

| | | | |
|---|---|---|---|
| 6,560,308 B1 * | 5/2003 | Zmora | 378/4 |
| 6,928,137 B2 * | 8/2005 | Bruder et al. | 378/4 |
| 7,822,171 B2 * | 10/2010 | Bontus et al. | 378/11 |
| 2005/0286749 A1 * | 12/2005 | De Man et al. | 382/131 |
| 2006/0104407 A1 * | 5/2006 | Zamyatin et al. | 378/4 |
| 2006/0182216 A1 * | 8/2006 | Lauritsch et al. | 378/4 |

OTHER PUBLICATIONS

Zou et al., Reduction of the streak artifacts in circular cone beam CT using scanograms, Conference date Oct. 26, 2007, IEEE Nuclear Science Symposium Conference, INSPEC Accession No. 9891827.*

* cited by examiner

*Primary Examiner* — Toan Ton
*Assistant Examiner* — John Corbett
(74) *Attorney, Agent, or Firm* — Oblon, Spivak, McClelland, Maier & Neustadt, L.L.P.

(57) ABSTRACT

A computed tomography apparatus and method using line data estimated from circle data and scanogram data. An image of a subject is reconstructed using the circle data and the estimated line data. The circle data and scanogram data may be weighted in estimating the line data. The apparatus and method are useful in diminishing or eliminating streak artifacts in reconstructed images such as images including the spine.

30 Claims, 12 Drawing Sheets

US 8,315,351 B2

SYSTEM AND METHOD FOR TOMOGRAPHIC RECONSTRUCTION UTILIZING CIRCULAR TRAJECTORY AND SCANOGRAM TO REDUCE ARTIFACTS

CROSS-REFERENCE TO RELATED APPLICATIONS

This application is a Continuation of and claims the benefit of priority under 35 U.S.C. §120 from U.S. Ser. No. 12/238,079, filed Sep. 25, 2008, and claims the benefit of priority under 35 U.S.C. §119(e) from 61/001,110, filed Oct. 31, 2007, the entire contents of which are incorporated herein by reference.

BACKGROUND OF THE INVENTION

1. Field of the Invention

The present invention relates to computed tomographic (CT) imaging, and in particular to CT imaging using scanograms to estimate line data from circular scans.

2. Discussion of the Background

In three-dimensional (3D) cone-beam computed tomography, the circular scan is widely used because of its convenience. It is well known that the projection data acquired from a cone-beam circular scan are not sufficient for volumetric reconstruction. The so-called cone-beam artifacts are found in the reconstructed images from circle-only cone-beam scan data. The low frequency shadow artifacts can be reduced by interpolation in the radon space. The high frequency artifacts due to the longitudinal abrupt change in the imaged subject are difficult to handle. A typical high frequency cone-beam artifact is the streaks off spines.

To eliminate the cone beam artifacts in circular cone-beam scans, an additional line scan, arc scan, or helical scan is usually performed to make the data complete for the volumetric reconstruction. The additional scan may increase the complexity of the scan protocol and increase the scan time and radiation dose.

SUMMARY OF THE INVENTION

An embodiment of the apparatus according to the invention may include an x-ray source, an x-ray detector disposed to receive x-rays from the x-ray source, a unit to collect circle data and scanogram data, and a processing unit for estimating line data from the circle data and the scanogram data and for performing reconstruction of an image using the circle data and the estimated line data.

An embodiment of the method according to the invention may include exposing a subject to x-rays, collecting circle data, collecting scanogram data, estimating line data using the circle data and the scanogram data, and reconstructing an image of the subject using the estimated line data and the circle data.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
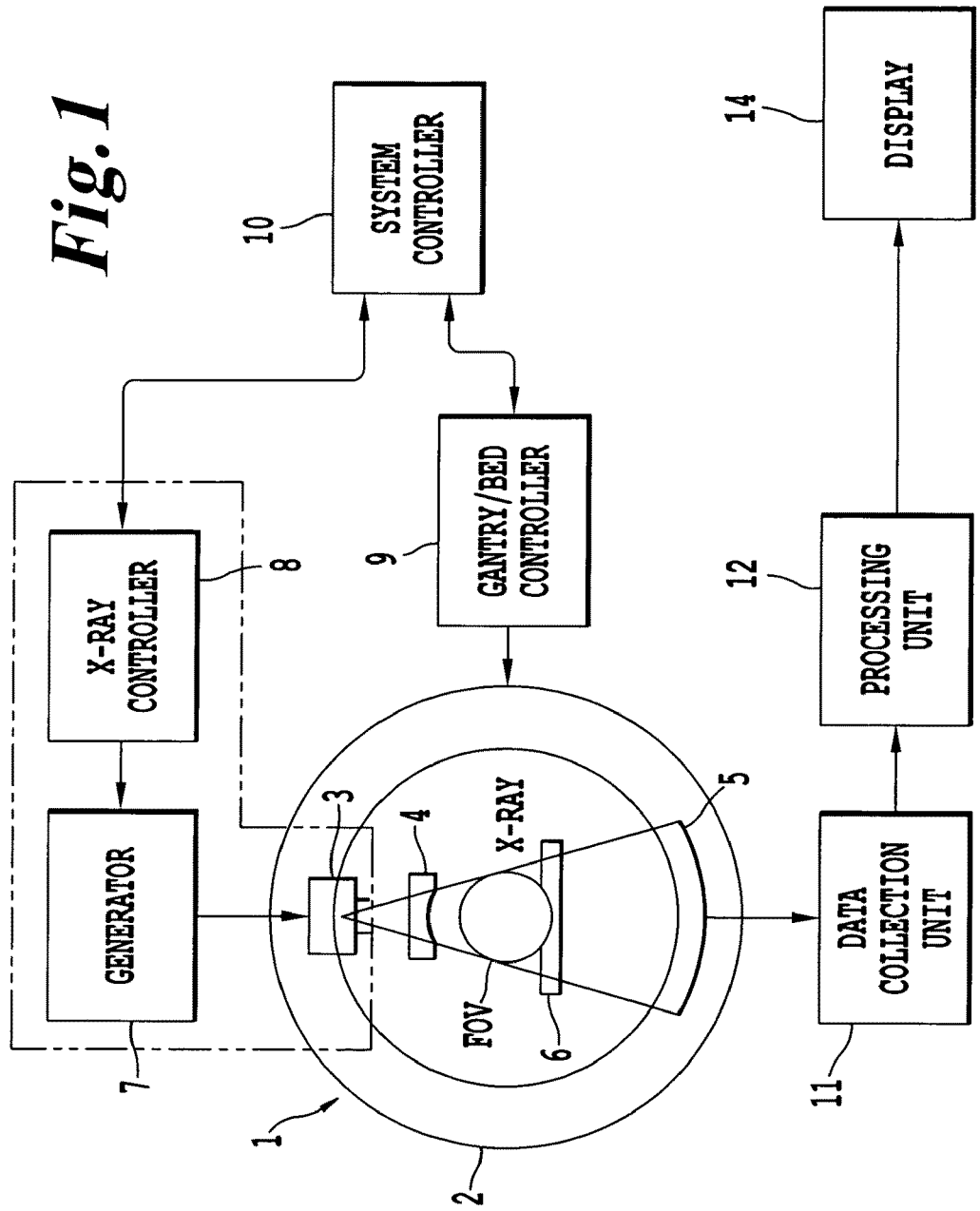
FIG. 1 is a diagram of a system according to the invention.

FIG. 1 shows an x-ray computed topographic imaging device according to the present invention. The projection data measurement system constituted by gantry 1 accommodates an x-ray source 3 that generates a cone-beam of x-ray flux approximately cone-shaped, and a two-dimensional array type x-ray detector 5 consisting of a plurality of detector elements arranged in two-dimensional fashion, i.e., a plurality of elements arranged in one dimension stacked in a plurality of rows. X-ray source 3 and two-dimensional array type x-ray detector 5 are installed on a rotating ring 2 in facing opposite sides of a subject, who is laid on a sliding sheet of a bed 6. Two-dimensional array type x-ray detector 5 is mounted on rotating ring 2. Each detector element will correspond with one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 with the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 and x-rays are emitted continuously or intermittently at fixed angular intervals from x-ray source 3.

The output signal of two-dimensional array type x-ray detector 5 is amplified by a data collection unit 11 for each channel and converted to a digital signal, to produce projection data. The projection data that is output from data collection unit 11 is fed to processing unit 12. Processing unit 12 performs various processing using the projection data. Unit 12 performs line data estimation (as described in more detail below, filtering, backprojection and reconstruction. Unit 12 determines backprojection data reflecting the x-ray absorption in each voxel. In the circular scanning system using a cone-beam of x-rays as in the first embodiment, the imaging region (effective field of view) is of cylindrical shape of radius R centered on the axis of revolution. Unit 12 defines a plurality of voxels (three-dimensional pixels) in this imaging region, and finds the backprojection data for each voxel. The three-dimensional image data or tomographic image data compiled by using this backprojection data is sent to display device 14, where it is displayed visually as a three-dimensional image or tomographic image.

Circle data is obtained by circular (helical) scans of the x-ray source. The line data for reconstruction is estimated from the circle data using the scanogram. A scanogram is an image obtained by moving the patient through the CT gantry through the plane of the x-ray source and detectors while x-ray projection measurements are made at a fixed source angular position. The image which is obtained in this manner is similar in general appearance to a conventional projection radiography image. Note that the scanogram is obtained with a very narrow cone beam, that is, only a few (in the order of 2 to 4) detector rows are utilized. On the other hand, circular data or true line data is collected with wide (full) cone angle, when up to several hundred detector rows may be utilized. Note that for exact reconstruction both circular and line data are necessary. An advantage of this invention is to avoid the line scan; instead, the unmeasured line data are estimated using available circle and scanogram data. Note that scanogram data is almost always available in clinical scans because it is applied before the patient scan for patient positioning.

Figure 2:
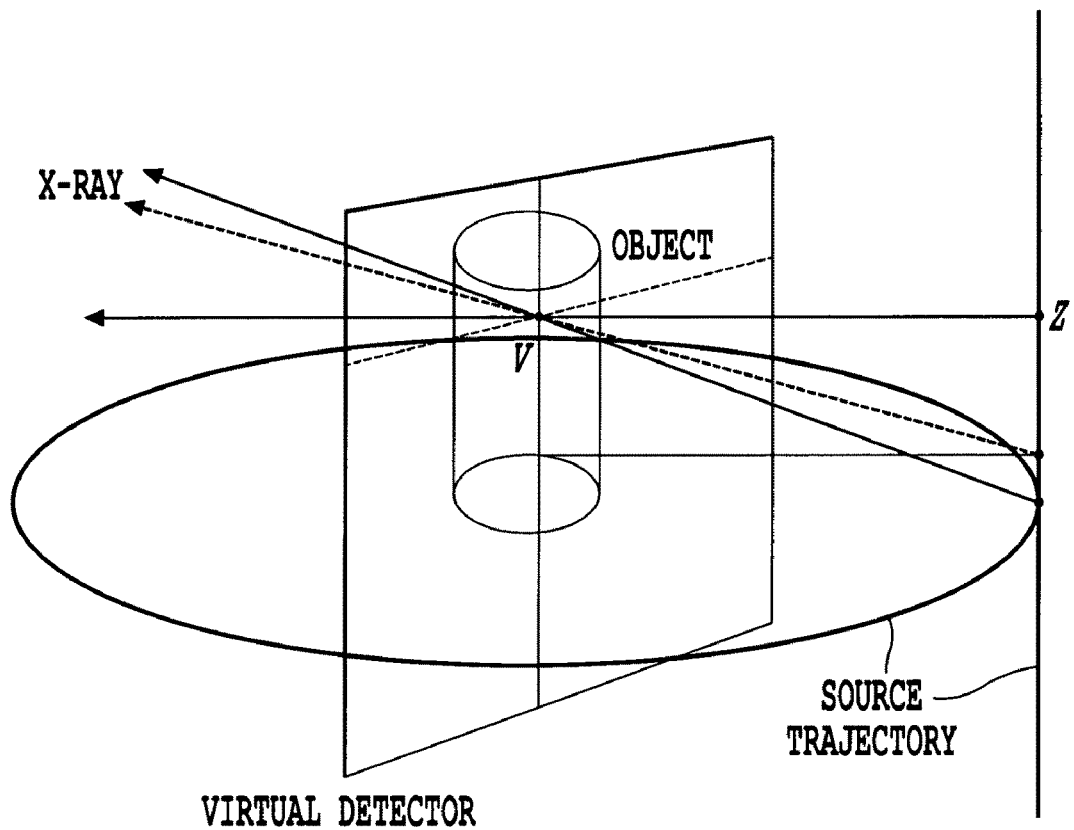
FIG. 2 is a diagram of the geometry for the circle scans and scanogram.

FIG. 2 illustrates the geometry. Circle data and the scanogram are obtained. The circle data can be parameterized as $P_C(u, v, \lambda)$, where $(u, v)$ are coordinates on the detector and $\lambda$ indicates the view (source rotation, projection) angle. Here v is the vertical detector coordinate and u is the horizontal detector coordinate; on the flat detector axis u is given by a straight line with equi-spaced linear grid; on the cylindrical detector axis u represents fan beam angle and is given by the equiangular grid. Source to detector distance is denoted SDD, or R. The line data $P_L(u, v, h)$ can be parameterized by detector coordinates, $(u, v)$, and the virtual (estimated) line source position, h. Only the case where h>0 is described. However, the case where h<0 is treated likewise. Note that h<2W, where W is the detector half-width. The line data can be estimated as a weighted sum of circle data and the scanogram:

$$P_L(u, v, h) = \frac{v}{v+h} P_C(u, v+h, \lambda_0) + \frac{h}{v+h} P_S(u, v+h) \quad (1)$$

where $P_s(u, z)$ indicates the scanogram, and $\lambda_0$ is the angular position at which line is attached to the circle. For v>0 and v<0, Eq. (1) represents a linear interpolation and extrapolation, respectively.

Figure 3A:
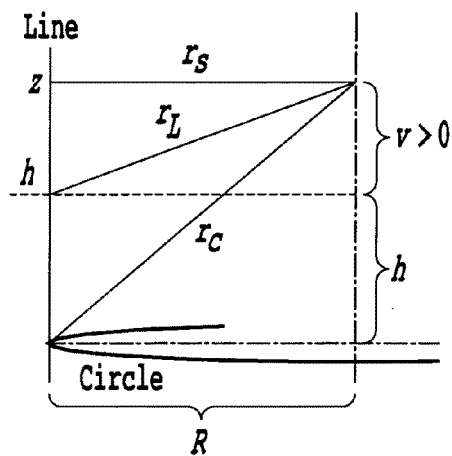
FIGS. 3A and 3B are diagrams illustrating estimating data line rays.
Figure 3B:
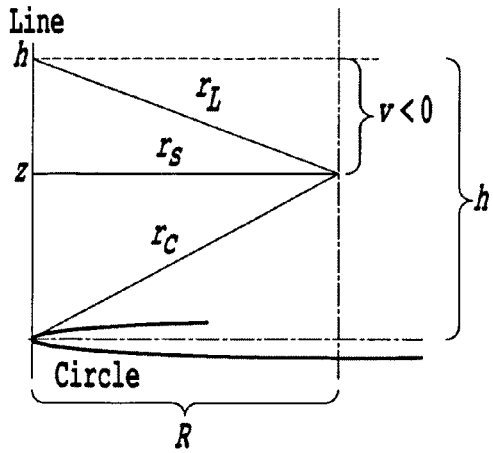

In general, there are two different cases to estimate the ray $(u, v)$ of the line data at h, depending on whether v>0 or v<0, illustrated by FIGS. 3A and 3B, respectively. The ray $r_L$ is the unmeasured line data ray $(\gamma, v)$ that is to be estimated. Rays, $r_C$ and $r_S$, are the measured rays from the circle and scanogram data, respectively. In FIG. 3A the measured rays are chosen in such way that they intersect the unmeasured ray at the virtual detector plane. Note that the ray $r_C$ is given by $(\gamma, v)$, where z=h+v, and $r_S$ is given by the source position z and fan angle $\gamma$.

Figure 4:
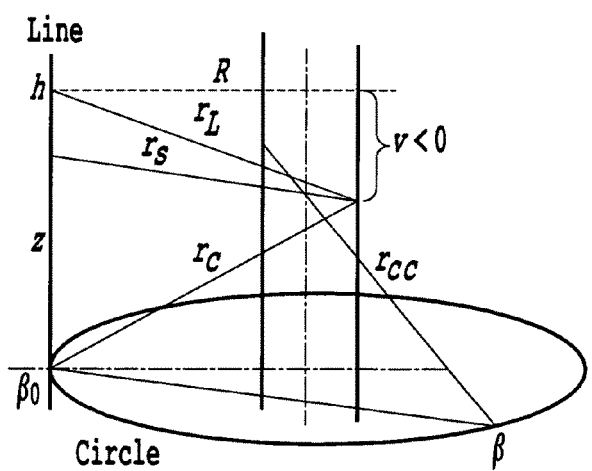
FIG. 4 is a diagram illustrating estimating data line rays using complementary data line rays.

Turning to the case illustrated in FIG. 3B, it can be seen from the figure that the ray $r_L$ cannot be interpolated between rays $r_C$ and $r_S$. (The ray $r_C$ is not close to $r_L$). Therefore, the complementary circle ray $r_{CC}$ is used, and is illustrated in FIG. 4. The source position for $r_{CC}$ is $\lambda=\lambda_0+\pi-2\gamma$, where $\lambda_0$ is the line angular position. Ray $r_{CC}$ is chosen in such way that it intersects $r_L$ midway between $\lambda$ and $\lambda_0$.

$$P_L(u, v, h) = \quad (2)$$
$$\begin{cases} w_1 P_C(u, v+h, \lambda_0) + (1-w_1)P_S(u, v+h), & \text{if } v > 0 \\ w_2 P_C(-u, v'+h, \lambda_0+\pi-2\gamma) + (1-w_2)P_S(u, v+h), & \text{if } v < 0 \end{cases}$$

where $$w_1 = \frac{v}{v+h} \text{ for both cylindrical and flat detectors} \quad (3)$$

$$w_2 = -\frac{2v\cos u}{h} \text{ for the cylindrical detector} \quad (4A)$$

$$w_2 = -\frac{2v}{h} \frac{SDD^2}{SDD^2 + u^2} \text{ for the flat detector} \quad (4B)$$

$$v' = \frac{v}{\cos^2 u} \text{ for the cylindrical detector} \quad (5A)$$

$$v' = v\sqrt{\frac{SDD^2 + u^2}{SDD^2}} \text{ for the flat detector} \quad (5B)$$

Note that equations (3)-(4) represent linear weighting between circle data and scanogram. In general, other weights are also possible. For example, the following polynomial weighting may be used:

$w_{1S}=3w_1^2-2w_1^3$.

$w_{2S}=3w_2^2-2w_2^3$.

Figure 5:
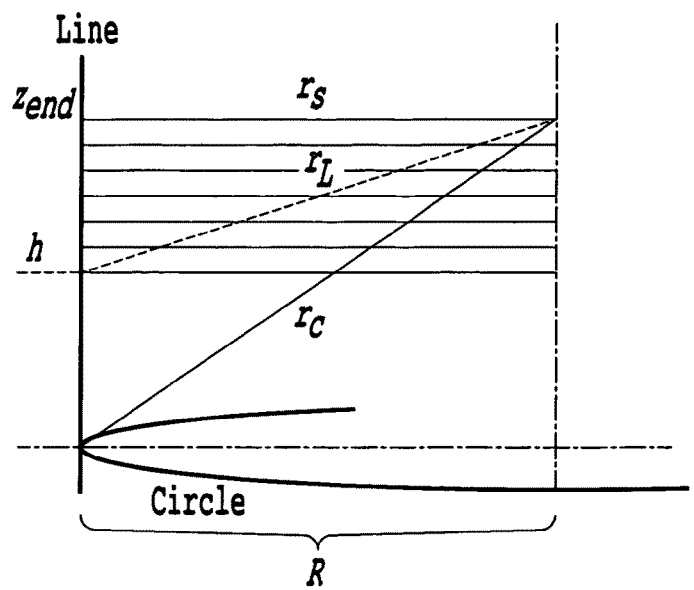
FIG. 5 is an image of estimating line data using multiple scanogram rays.

In the main embodiment, only one scanogram ray is used in the weighted sum (1) or (2). Alternatively, a plurality of scanogram rays can be used to estimate each missing line ray, as shown in FIG. 5.

Once line data is estimated using the proposed method, any suitable reconstruction algorithm can be used. There two classes of suitable algorithms: filtered-backprojection (FBP) and derivative backprojection filtration (BPF). Example of an FBP algorithm is Katsevich line+circle algorithm (A. Katsevich, Image reconstruction for the circle and line trajectory, Physics in Medicine and Biology, vol. 49, pp. 5059-5072, 2004.) Another example of FBP algorithm that can be applied to circular data only is Feldkamp-type reconstruction (L. A. Feldkamp, L. C. Davis and J. W. Kress, Practical cone beam algorithm, Journal of Optical Society of America, vol. 1 (6), pp. 612-619, June 1984.)

Also, reconstruction algorithms may use full revolution of circular data (full scan, or 1PI mode), or partial revolution (short, or half scan, or 2PI mode). Both types can be used with the proposed invention.

Figure 6:
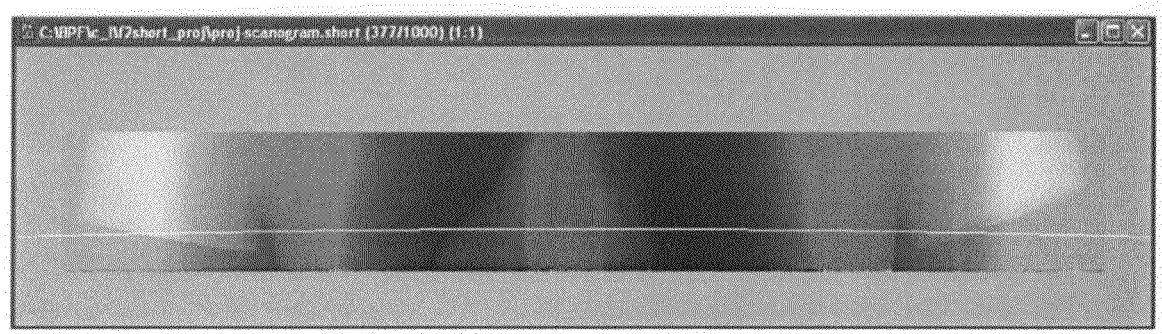
FIG. 6 is an image of estimated line data.

FIG. 6 illustrates the estimated line data at one view. A chest phantom is exposed to x-ray to produce projection data. The bright line indicates the projection of the circular trajectory. Only the data above the line contribute to the reconstruction. The data below the line look noisy but do not affect the reconstructed images.

Empirical Weighting Factor

Figure 7:
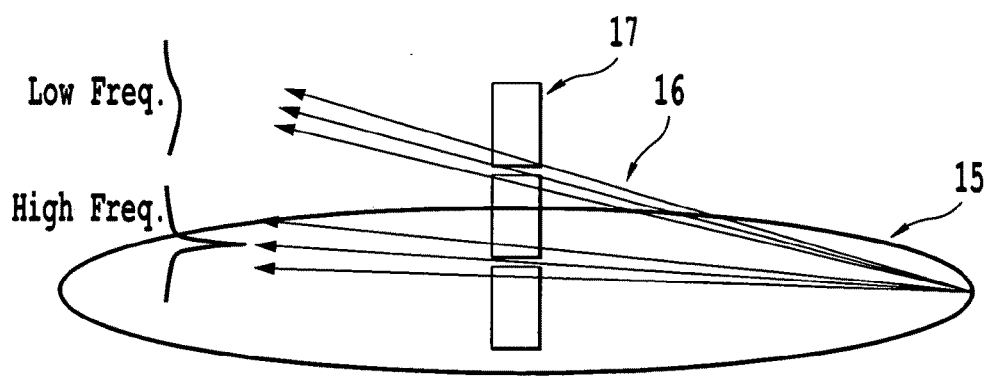
FIG. 7 is a diagram illustrating a weighting factor used in the method according to the invention.

The method according to the invention is particularly useful in reducing streak artifacts. The streak artifacts off the spine are caused by the high frequency components near the joints in the circle data. The high frequency components can be compensated by line data in exact circle-line algorithms and the streak artifacts can be avoided. FIG. 7 show x-rays 16 along trajectory 15 passing through the spine 17. The joint close to the middle plane yields more high frequency data than the joints far from the middle plane.

On the other hand, in the line data each joint is equivalent in the sense of high frequency components. These features for the circle data and the line data imply that the high frequency components in the line data related to the joint close to the middle plane tend to compensate their counterparts in the circle data. The high frequency components in the line data related to the joints far from the middle plane have no their counterparts in the circle data. Therefore they must cancel each other within the line data. The estimated data from the scanogram and the circle data do contain errors, especially in the high frequency components. It may result in additional streak artifacts near the joint far from the middle plane.

Figure 8A:
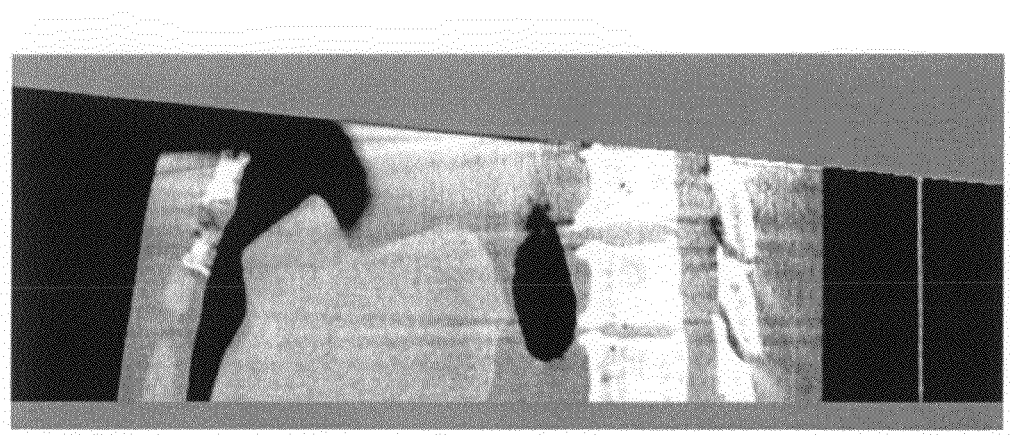
FIG. 8A is a reconstructed image above the middle plane from circle data only.
Figure 8B:
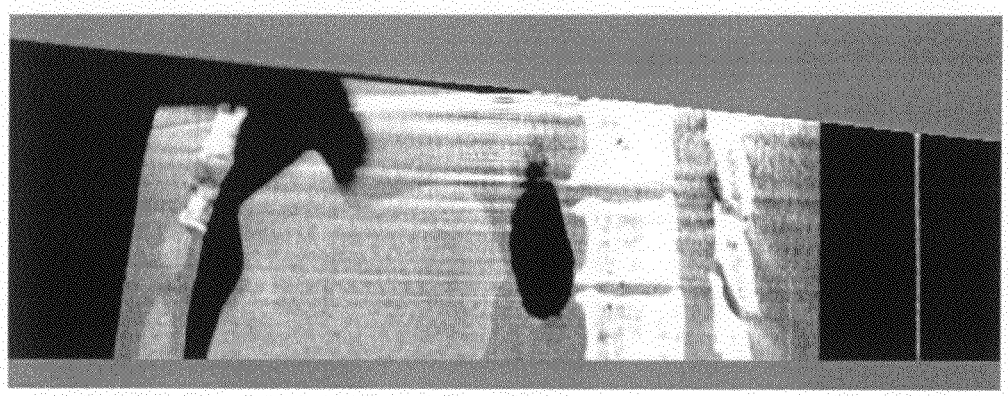
FIG. 8B is a reconstructed image above the middle plane from circle data and estimated line data.
Figure 8C:
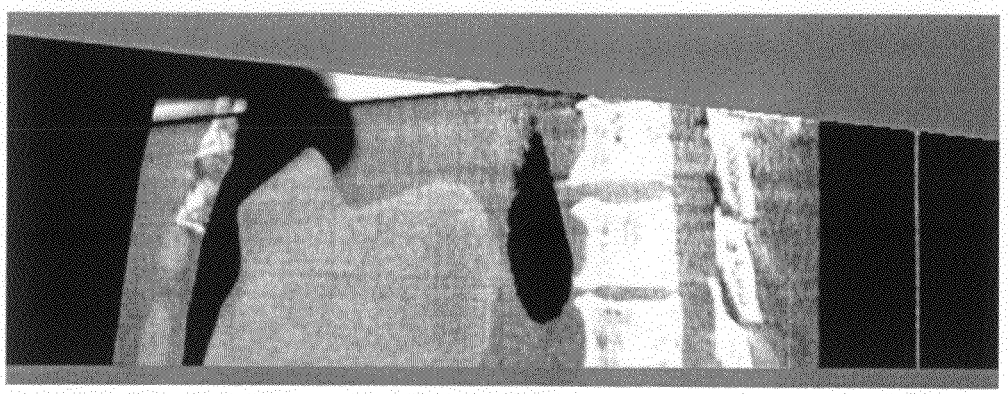
FIG. 8C is a reconstructed image above the middle plane from circle data and estimated line data with weighting.

A weighting factor can be introduced to improve the reconstructed images by reducing such streaks. An empirical weighting factor $$\frac{1}{2}\left(1 + \cos\frac{h\pi}{d}\right)$$

is introduced to Eq. (1) or (2) to reduce the artifact:

$$P_{LF}(u, v, h) = \frac{1}{2}\left(1 + \cos\frac{h\pi}{d}\right) \times P_L(u, v, h) \quad (6)$$

where d is an adjustable parameter. The factor reduces the contribution of the line data away from the middle plane. The parameter d is determined empirically and ranges from 1 to 100. FIG. 8 shows the effect of empirical weighting factor. FIG. 8A shows a slice of image above middle plane reconstructed from only the circle data. It can be seen that strong streak artifacts appear off the joint close to middle plane (at bottom of the image) and less streaks can be seen near the joint far from the middle plane. As shown in FIG. 8B, the streak artifacts close to the middle plane are reduced by use of the estimated line data from the scanogram but more and intense streaks appear off the second joint from the middle plane that are caused by the errors in the estimated line data. FIG. 8C shows the reconstructed image with the empirical weighting factor. The streak artifacts are reduced significantly but some of them are still visible.

Local Smoothing

Figure 9:
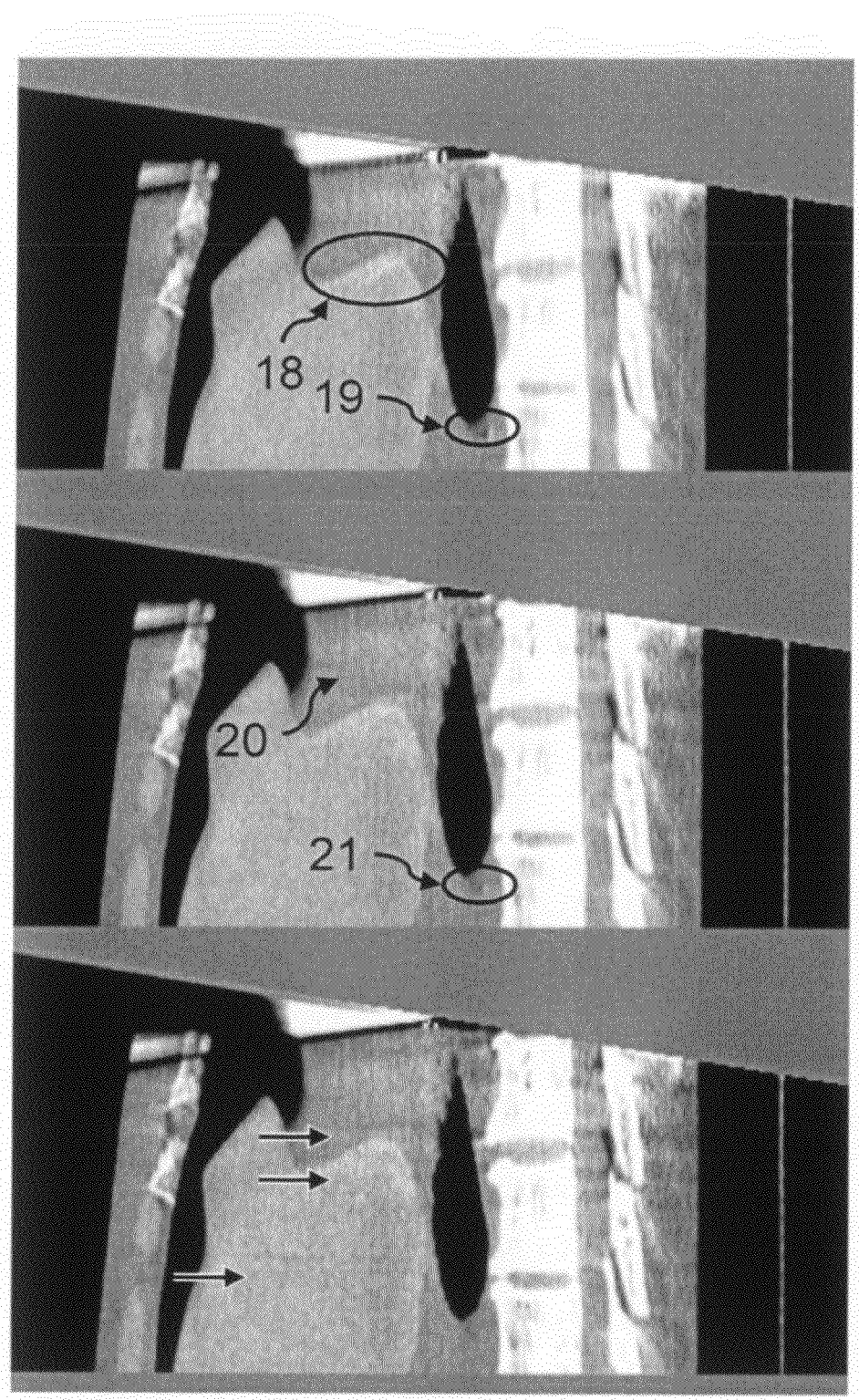
FIG. 9 shows reconstructed images from the locally smoothed projections of measured circle and estimated line data.

As the streak artifacts off spines are caused by the high frequency components in the projection data near spine joints, the artifacts may be also reduced by eliminating the high frequency components. A simple method to reduce the high frequency components is running average. The average is performed only vertically and in the vicinity of spines, and is called local smoothing. FIG. 9 shows the reconstructed images from the locally smoothed projections of measured circle and estimated line data. Three tests were performed with running average pixel numbers of 9, 5, and 3, as an example; other values are also acceptable. The streak artifacts in the reconstructed images are reduced significantly. There is some blurring in the spine region. On the image with 9-pixel running average (top), a bright spot and a dark spot indicated by the circles 18 and 19, respectively, can be observed. On the image with 5-pixel running average (middle), a dark band (arrow 20) and a dark spot 21 are visible. On the image with 3-pixel running average, a dark band and a few streaks are marked with arrows but are dimly visible. Overall, for this type of image the 5-pixel running average produces the best quality image.

Figure 10:
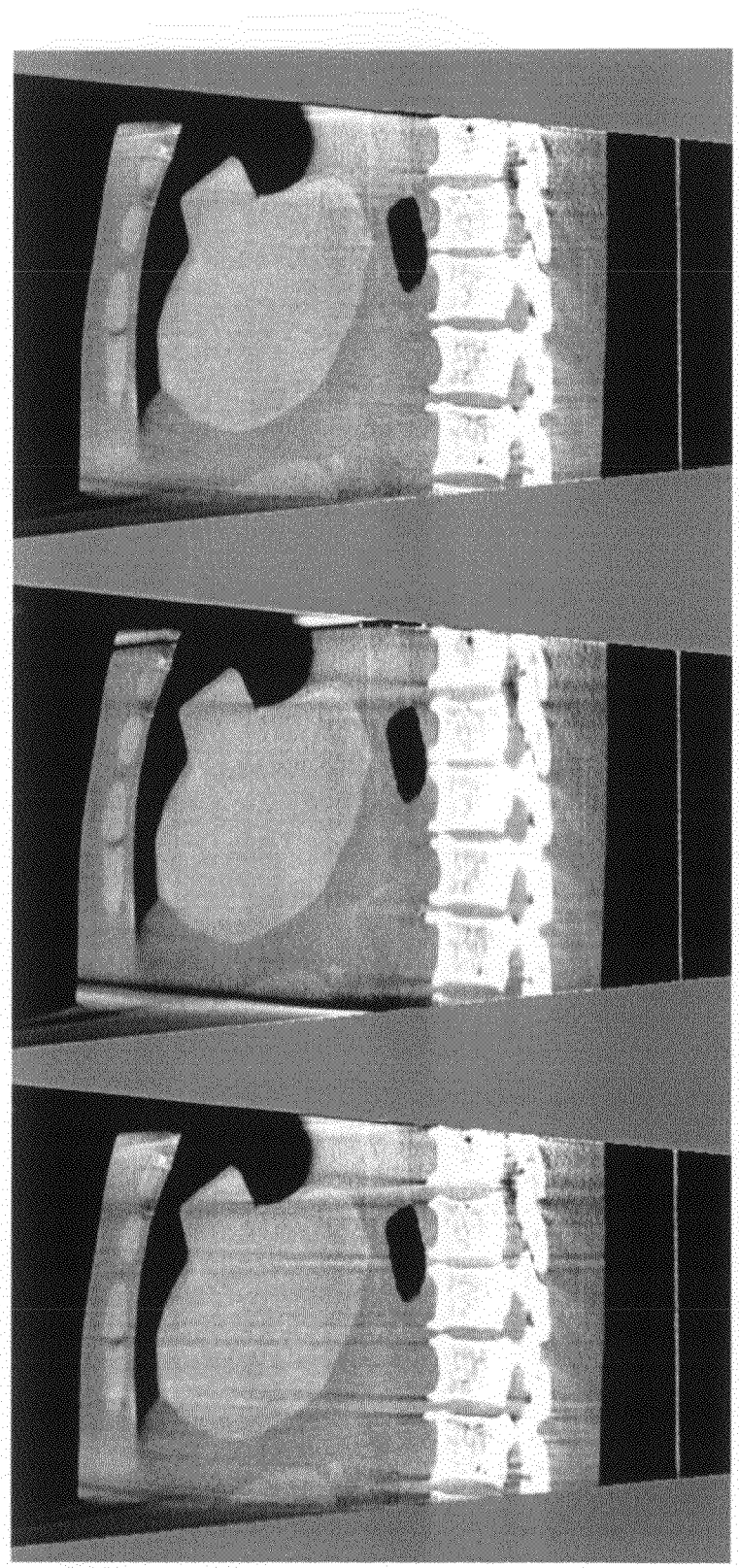
FIG. 10 shows reconstructed images of a sagittal slice for real circle and line data (top), real circle data and estimated line data (middle) and circle data only (bottom)

To examine the image quality in the volume, images were reconstructed in both upper and lower portions of the circle trajectory using the method according to the invention with local smoothing. FIG. 10 shows the images on the median plane. The quality of images from real circle and line data (top) and from real circle and estimated line data (middle) is comparable. They are much better than that from circle-only data (bottom).

Figure 11A:
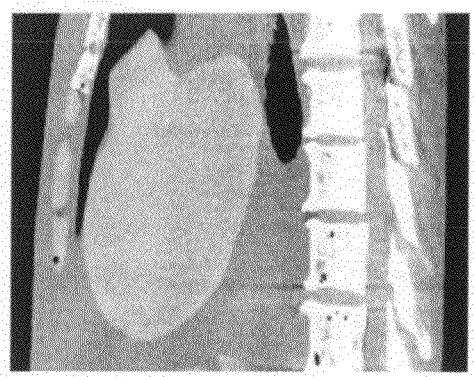
FIGS. 11A-D are chest images prepared with circle data only, circle and line data, circle and scanogram data with local smoothing, and circle and scanogram data and adaptive z-filtering, respectively.
Figure 11B:
Figure 11C:
Figure 11D:
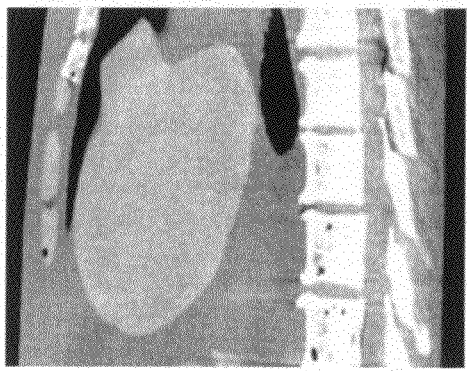
Figure 12A:
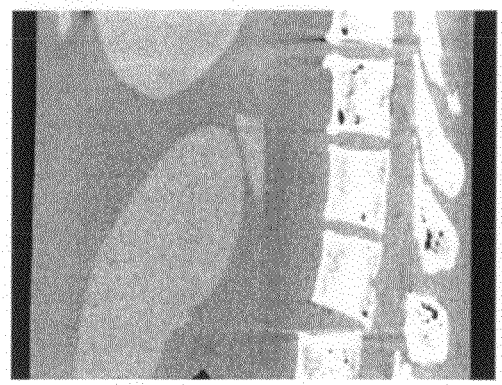
FIGS. 12A-D are abdomen images prepared with circle data only, circle and line data, circle and scanogram data with local smoothing, and circle and scanogram data and adaptive z-filtering, respectively.
Figure 12B:
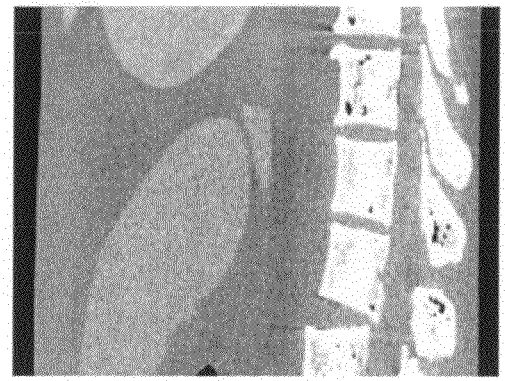
Figure 12C:
Figure 12D:
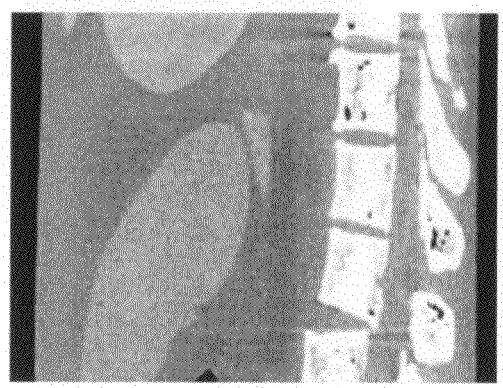
Figure 13A:
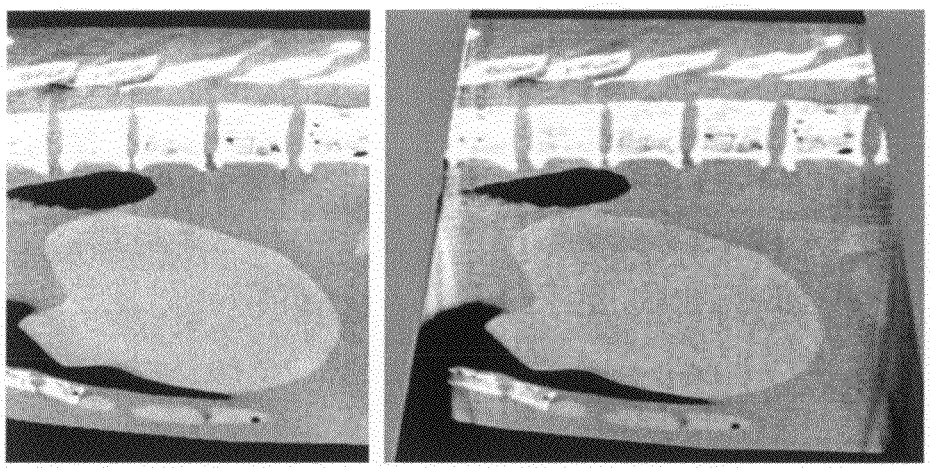
FIGS. 13A-C are chest images are reconstructed using filtered backprojection (top images) and BPF (bottom images)
Figure 13B:
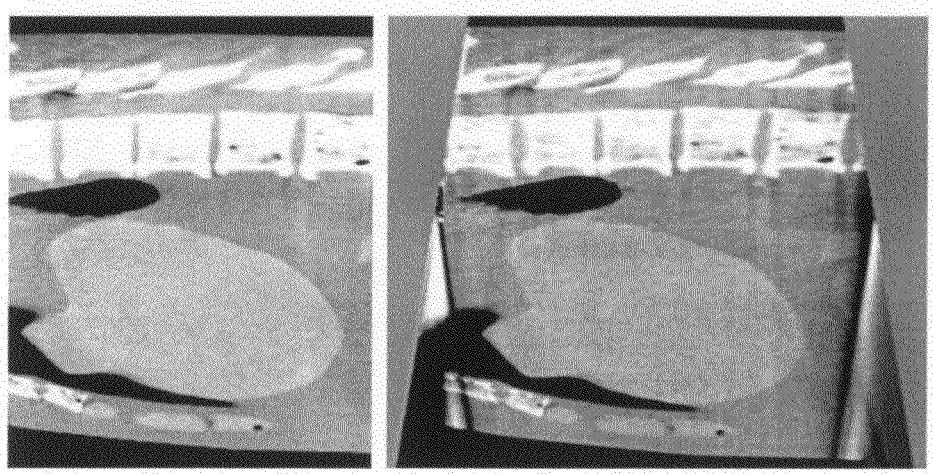
Figure 13C:
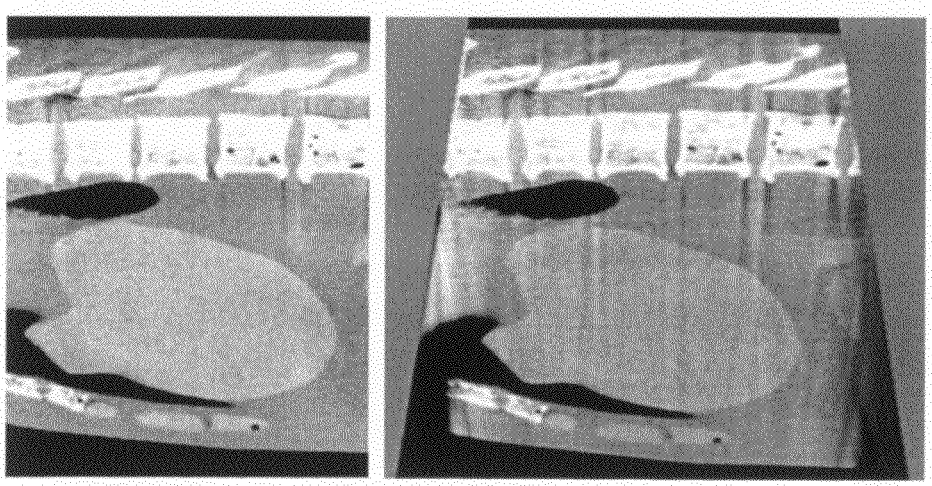
Figure 14C:
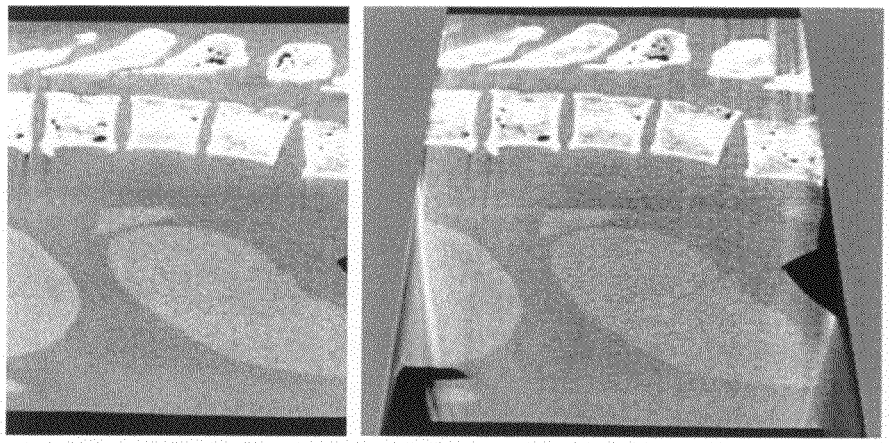
FIGS. 14A-C are abdomen images reconstructed using filtered backprojection (top images) and BPF (bottom images).
Figure 14B:
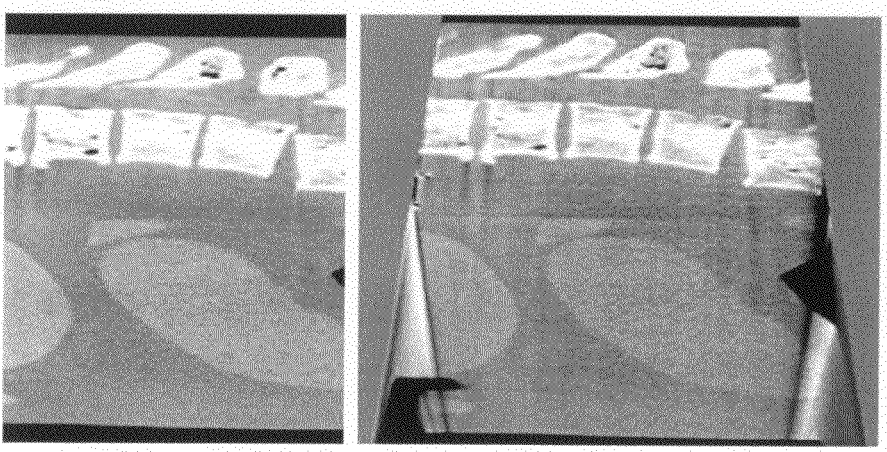
Figure 14A:
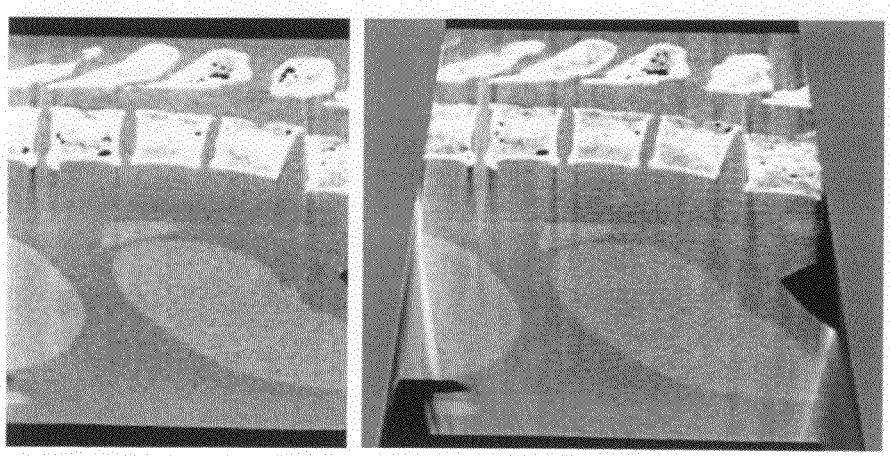

In a further modification, adaptive z-filtering is used instead of the local smoothing. Here the strength of smoothing in the z-direction is adapted to the data z-gradient, that is, for structures with sharper z-gradient more smoothing is applied, and vice versa. Chest region images comparing the adaptive z-filtering and local smoothing are shown in FIGS. 11A-D. FIG. 11A is an image reconstructed using only the circle data, while FIG. 11B is an image reconstructed using circle and line data. FIG. 11C is an image reconstructed using the circle and scanogram data and local smoothing as described above. FIG. 11D is an image reconstructed using the circle and scanogram data and adaptive z-filtering. Strong and weak streak artifacts can be seen at the first and second joints in the circle-only image (FIG. 11A). In the circle-line image (FIG. 11B), the strong streaks are reduced significantly and the weak streaks disappear. The two images reconstructed according to the invention (FIGS. 11C-D) using the circle and scanogram data appear similar. The strong streaks are reduced and the weak streaks disappear. Compared with that of the circle-line, there is only a small amount of blurring. The images reconstructed according to the invention are good quality.

Similar results are found for abdomen images. FIGS. 12A-D illustrate images reconstructed using only circle data, circle and line data, circle and scanogram data using local smoothing according to the invention, and circle and scanogram data using adaptive z-filtering according to the invention. Strong streak artifacts can be seen at the first and fourth joints in the circle-only image (FIG. 12A) and the weak streaks appear near the third joint. In the circle-line image (FIG. 12B), the strong streaks are reduced and the weak streaks disappear. The two images using the circle and scanogram data (FIGS. 12C-D) appear similar. The strong streaks are reduced and the weak streaks disappear. Compared with that of the circle-line (FIG. 12B), there is only a small amount of blurring. Again, good quality images can be reconstructed.

A comparison of two reconstruction techniques was made. Referring to FIGS. 13A-C and 14A-C, chest and abdomen images are reconstructed using filtered backprojection (FBP) (top images) and backprojection-filtration (BPF) (bottom images). For the chest images, in the circle-only images (FIG. 13A), the streak artifacts from BPF are stronger than that from FBP. For the chest images using circle-scanogram data (FIG. 13B) and circle-line data (FIG. 13C), the images of FBP appear to be of slightly better quality than those of BPF. Note that the reconstruction of BPF did not include data corrections and only use short-scan circle data.

Similar results are obtained for the abdomen images. In the circle-only images (FIG. 14A), the streak artifacts from BPF are stronger than that from FBP. For the abdomen images using circle-scanogram data (FIG. 14B) and circle-line data (FIG. 14C), the images of FBP appear to be of slightly higher quality than those of BPF. Again, Note that the reconstruction of BPF did not include data corrections and only use short scan circle data The present invention may be implemented in software or in hardware. In particular the operation of the processing unit described above can be carried out as a software program run on a microprocessor or a computer. The software can be stored on a computer-readable medium and loaded into the system.

Numerous other modifications and variations of the present invention are possible in light of the above teachings. It is therefore to be understood that within the scope of the appended claims, the invention may be practiced otherwise than as specifically described herein.

The invention claimed is:

1. A computed-tomography apparatus, comprising:
   an x-ray source;
   an x-ray detector disposed to receive x-rays from said x-ray source;
   a unit to collect circle data and scanogram data;
   a processing unit for estimating line data from said circle data and said scanogram data and for performing reconstruction of an image using said circle data and said estimated line data,
   wherein said processing unit is configured to estimated said line data using:

$$P_L(u, v, h) = \frac{v}{v+h} P_C(u, v+h, \lambda_0) + \frac{h}{v+h} P_S(u, v+h)$$

where $P_C(u, v, \lambda)$ is said circle data, $P_S(u, z)$ is said scanogram data, $(u, v)$ are detector coordinates, $h$ is an estimated line source position, $z=v+h$, $\lambda$ is a view angle and $\lambda_0$ is a line angular position.

2. An apparatus as recited in claim 1, wherein said processing unit is configured to estimate said line data using:

$$P_L(u, v, h) = \begin{cases} w_1 P_C(u, v+h, \lambda_0) + (1-w_1) P_S(u, v+h), & \text{if } v > 0 \\ w_2 P_C(-u, v'+h, \lambda_0 + \pi - 2\gamma) + (1-w_2) P_S(u, v+h), & \text{if } v < 0 \end{cases}$$

$$w_1 = \frac{v}{v+h}$$

$$w_2 = -\frac{2v\cos u}{h}, \quad v' = \frac{v}{\cos^2 u} \text{ for a cylindrical detector}$$

$$w_2 = -\frac{2v}{h} \frac{SDD^2}{SDD^2 + u^2}, \quad v' = v\sqrt{\frac{SDD^2 + u^2}{SDD^2}} \text{ for a flat detector}$$

where $P_C(u, v, \lambda)$ is said circle data, $P_S(u, z)$ is said scanogram data, SDD is the source to detector distance, and $w_1$ and $w_2$ are weighting factors.

3. An apparatus as recited in claim 2, wherein said processing unit is further configured to estimate said line data using $$P_{LF}(u, v, h) = \frac{1}{2}\left(1 + \cos\frac{h\pi}{d}\right) \times P_L(u, v, h).$$

4. An apparatus as recited in claim 2, wherein said weighting factors comprise:

$$w_{1S} = 3w_1^2 - 2w_1^3, \text{ and}$$

$$w_{2S} = 3w_2^2 - 2w_2^3.$$

5. An apparatus as recited in claim 1, wherein said processing unit is further configured to estimate said line data using $$P_{LF}(u, v, h) = \frac{1}{2}\left(1 + \cos\frac{h\pi}{d}\right) \times P_L(u, v, h).$$

6. An apparatus as recited in claim 1, wherein said processing unit is configured to estimate said line data using multiple scanogram rays for each estimated line ray.

7. An apparatus as recited in claim 1, wherein said processing unit is configured to estimate said line data using one of local smoothing and adaptive filtering.

8. An apparatus as recited in claim 1, wherein said processing unit is configured to reconstruct said image using one of filtered backprojection type reconstruction and backprojection filtration type reconstruction.

9. An apparatus as recited in claim 1, wherein said processing unit is configured to reconstruct said image using full revolution circular data.

10. An apparatus as recited in claim 1, wherein said processing unit is configured to reconstruct said image using partial revolution circular data.

11. A computed tomography method, comprising:
    exposing a subject to x-rays;
    collecting circle data;
    collecting scanogram data;
    estimating line data using said circle data and said scanogram data using:

$$P_L(u, v, h) = \frac{v}{v+h} P_C(u, v+h, \lambda_0) + \frac{h}{v+h} P_S(u, v+h)$$

where $P_C(u, v, \lambda)$ is said circle data, $P_S(u, z)$ is said scanogram data, $(u, v)$ are detector coordinates, $h$ is an estimated line source position, $z=v+h$, $\lambda$ is a view angle and $\lambda_0$ is a line angular position; and reconstructing an image of said subject using said estimated line data and said circle data.

12. A method as recited in claim 11, comprising estimating said line data using:

$$P_L(u, v, h) = \begin{cases} w_1 P_C(u, v+h, \lambda_0) + (1-w_1) P_S(u, v+h), & \text{if } v > 0 \\ w_2 P_C(-u, v'+h, \lambda_0 + \pi - 2\gamma) + (1-w_2) P_S(u, v+h), & \text{if } v < 0 \end{cases}$$

$$w_1 = \frac{v}{v+h}$$

$$w_2 = -\frac{2v\cos u}{h}, \quad v' = \frac{v}{\cos^2 u} \text{ for a cylindrical detector}$$

$$w_2 = -\frac{2v}{h} \frac{SDD^2}{SDD^2 + u^2}, \quad v' = v\sqrt{\frac{SDD^2 + u^2}{SDD^2}} \text{ for a flat detector}$$

where $P_C(u, v, \lambda)$ is said circle data, $P_S(u, z)$ is said scanogram data, SDD is the source to detector distance, $w_1$ and $w_2$ are weighting factors.

13. A method as recited in claim 12, comprising estimating said line data using $$P_{LF}(u, v, h) = \frac{1}{2}\left(1 + \cos\frac{h\pi}{d}\right) \times P_L(u, v, h).$$

14. An method as recited in claim 12, wherein said weighting factors comprise $w_{1S} = 3w_1^2 - 2w_1^3$, and $w_{2S} = 3w_2^2 - 2w_2^3$.

15. A method as recited in claim 11, comprising estimating said line data using $$P_{LF}(u, v, h) = \frac{1}{2}\left(1 + \cos\frac{h\pi}{d}\right) \times P_L(u, v, h).$$

16. A method as recited in claim 11, comprising estimating said line data using multiple scanogram rays for each estimated line ray.

17. A method as recited in claim 11, comprising estimating said line data using one of local smoothing and adaptive filtering.

18. A method as recited in claim 11, wherein said reconstructing comprises one of filtered backprojection type reconstruction and backprojection filtration type reconstruction.

19. A method as recited in claim 11, wherein said reconstructing comprises reconstruction of full revolution circular data.

20. A method as recited in claim 11, wherein said reconstructing comprises reconstruction of partial revolution circular data.

21. A non-transitory computer readable-medium containing instructions that are executed by a computer to perform a method, comprising:
    collecting circle data from an x-ray scan of a subject;
    estimating line data using said circle data and said scanogram data using:

$$P_L(u, v, h) = \frac{v}{v+h}P_C(u, v+h, \lambda_0) + \frac{h}{v+h}P_S(u, v+h)$$

where $P_C(u, v, \lambda)$ is said circle data, $P_S(u, z)$ is said scanogram data, (u, v) are detector coordinates, h is an estimated line source position, z=v+h, $\lambda$ is a view angle and $\lambda_0$ is a line angular position; and
    reconstructing an image of said subject using said estimated line data and said circle data.

22. A medium as recited in claim 21, wherein said method comprises:
    estimating said line data using:

$P_L(u, v, h) =$ $\begin{cases} w_1 P_C(u, v+h, \lambda_0) + (1-w_1)P_S(u, v+h), & \text{if } v > 0 \\ w_2 P_C(-u, v'+h, \lambda_0 + \pi - 2\gamma) + (1-w_2)P_S(u, v+h), & \text{if } v < 0 \end{cases}$ $w_1 = \frac{v}{v+h}$ $w_2 = -\frac{2v\cos u}{h}, v' = \frac{v}{\cos^2 u}$ for a cylindrical x-ray detector $w_2 = -\frac{2v}{h}\frac{SDD^2}{SDD^2+u^2}, v' = v\sqrt{\frac{SDD^2+u^2}{SDD^2}}$ for a flat x-ray detector where $P_C(u, v, \lambda)$ is said circle data, $P_S(u, z)$ is said scanogram data, SDD is the source to detector distance, $w_1$ and $w_2$ are weighting factors.

23. A medium as recited in claim 22, wherein said method comprises:
    estimating said line data using $$P_{LF}(u, v, h) = \frac{1}{2}\left(1 + \cos\frac{h\pi}{d}\right) \times P_L(u, v, h).$$

24. A medium as recited in claim 21, wherein said method comprises:
    estimating said line data using $$P_{LF}(u, v, h) = \frac{1}{2}\left(1 + \cos\frac{h\pi}{d}\right) \times P_L(u, v, h).$$

25. A medium as recited in claim 22, wherein said weighting factors comprise $w_{1S} = 3w_1^2 - 2w_1^3$, and $w_{2S} = 3w_2^2 - 2w_2^3$.

26. A medium as recited in claim 21, wherein said method comprises estimating said line data using multiple scanogram rays for each estimated line ray.

27. A medium as recited in claim 21, wherein said method comprises estimating said line data using one of local smoothing and adaptive filtering.

28. A medium as recited in claim 21, wherein said reconstructing comprises one of filtered backprojection type reconstruction and backprojection filtration type reconstruction.

29. A medium as recited in claim 21, wherein said reconstructing comprises reconstruction of full revolution circular data.

30. A medium as recited in claim 21, wherein said reconstructing comprises reconstruction of partial revolution circular data.

* * * * *